(12) United States Patent
Nakamura et al.

(10) Patent No.: US 6,503,200 B2
(45) Date of Patent: Jan. 7, 2003

(54) ULTRASONIC DIAGNOSTIC APPARATUS

(75) Inventors: Mitsuyuki Nakamura, Yokohama (JP); Noboru Kosaka, Mitaka (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/795,354

(22) Filed: Mar. 1, 2001

(65) Prior Publication Data

US 2001/0034484 A1 Oct. 25, 2001

(30) Foreign Application Priority Data

Mar. 28, 2000 (JP) ........................................ 2000-087851

(51) Int. Cl.$^7$ ................................................. A61B 8/00
(52) U.S. Cl. ........................................................ 600/443
(58) Field of Search ............................... 600/437, 443, 600/447, 454–456; 73/625–626

(56) References Cited

U.S. PATENT DOCUMENTS

| | | | | |
|---|---|---|---|---|
| 4,534,221 A | * | 8/1985 | Fife et al. .................. | 73/626 |
| 5,072,735 A | * | 12/1991 | Okazaki et al. | |
| 5,379,642 A | * | 1/1995 | Reckwerdt et al. ........... | 73/625 |
| 5,608,690 A | * | 3/1997 | Hossack et al. ............. | 367/138 |
| 5,797,846 A | * | 8/1998 | Seyed-Bolorforosh et al. .. | 600/447 |
| 5,919,137 A | * | 7/1999 | Finger et al. ................ | 600/443 |
| 5,976,087 A | * | 11/1999 | Resnick et al. .............. | 600/443 |
| 6,113,544 A | * | 9/2000 | Mo ............................. | 600/447 |
| 6,123,670 A | * | 9/2000 | Mo ............................. | 600/447 |
| 6,146,300 A | * | 11/2000 | Tujino et al. ................ | 600/443 |

OTHER PUBLICATIONS

Patent Abstracts of Japan, vol. 018, No. 285 (c–1206), May 31, 1994 & JP 06 054850 A (Toshiba Corp.), Mar. 1, 1994.

* cited by examiner

Primary Examiner—Francis J. Jaworski
(74) Attorney, Agent, or Firm—Wenderoth, Lind & Ponack, L.L.P.

(57) ABSTRACT

The ultrasonic diagnostic apparatus of the present invention comprises an operation panel 11 through which different diagnostic conditions are set, a system controller 12 for controlling the frequency of the ultrasonic wave to be transmitted according to the field of view, a transmitting circuit 13 for transmitting ultrasonic wave, a receiving circuit 15 for receiving the reflected wave from an ultrasonic probe 14 to convert the reflected wave into an electric signal, an image processing unit 16 for applying the predetermined processing to the signal from the receiving circuit 15 and a display unit 17 for displaying tomographic image on the basis of the electric signal from the image processing apparatus 16.

10 Claims, 5 Drawing Sheets

ULTRASONIC DIAGNOSTIC APPARATUS

BACKGROUND OF THE INVENTION

The present invention relates to an ultrasonic diagnostic apparatus for transmitting an ultrasonic wave to a living body and receiving a wave reflected by the living body to produce a tomographic image from the reflected wave.

An ultrasonic diagnostic apparatus has been conventionally used for medical diagnosis for the purpose of producing organic information of a living body or a patient. This ultrasonic diagnostic apparatus transmits an ultrasonic pulse into an organ of the patient through an ultrasonic probe and receives the reflected wave from a boundary surface between tissues different in acoustic impedance through the ultrasonic probe to convert the reflected wave into an electric signal. Further, the ultrasonic diagnostic apparatus displays an ultrasonic tomographic image on a monitor on the basis of the electric signal.

In such a ultrasonic diagnostic apparatus, the depth from the organic surface in which an ultrasonic tomographic image can be produced, namely, a limit of visible depth becomes shallower the higher frequency of ultrasonic wave is used for diagnosis because an ultrasonic wave is heavily absorbed by the organ in proportional to the frequency of the ultrasonic wave. However, it is desirable to use a high frequency wave in order to produce an ultrasonic tomographic image of a high resolution.

In transmission of an ultrasonic wave, it is desirable to increase the frequency of the ultrasonic wave to be transmitted in order to increase the resolution of a target region for diagnosis. However, even if the depth set to be displayed on the monitor, namely, the depth of field of view is set deep, the limit of visible depth is constant because the frequency of the ultrasonic wave to be transmitted is constant.

Conventionally, the ultrasonic diagnostic apparatus as described in Japanese Patent Public Disclosure No. 6-54850 is well known. The construction of this apparatus is shown in FIG. 5. In FIG. 5, a system controller 112 controls a drive frequency for an ultrasonic probe 115 according to a focus position, a color display area or a Doppler signal detection position. According to this apparatus, the frequency of the ultrasonic wave is changed according to the focus position, the color display area or the Doppler signal detection position.

However, the conventional apparatus as set forth above has disadvantages that even if the depth of field of view is set deep in order to display the diagnostic target region, the visual depth limit does not change because the transmitting frequency does not change and as a result, it is difficult to produce organic information on the area surrounding the diagnostic target region.

Further, the conventional apparatus has disadvantages that even if the depth of field of view is set shallow in order to display the diagnostic target region, the resolution of the diagnostic target region does not change because the transmitting frequency does not change and as a result, it is difficult to produce an image of high resolution.

Further, the conventional apparatus has disadvantages that even if the enlargingly displayed area of field of view is set deep in order to enlargingly display the diagnostic target region, the visible depth limit does not change because the transmitting frequency does not change and as a result, it is difficult to produce organic information on the area surrounding the enlargingly displayed area of field of view.

Further, the conventional apparatus has disadvantages that even if the enlargingly displayed area of field of view is set shallow in order to enlargingly display the diagnostic target region, the resolution of the enlargingly displayed area of field of view does not change because the transmitting frequency does not change and as a result, it is difficult to produce an image of high resolution.

Further, the conventional apparatus has disadvantages that even if the field of view is changed, the transmitting frequency cannot be changed without changing the focus position, the color display area or the Doppler signal detection position in the field of view.

It is an object of the present invention to solve the problem set forth above in the prior art and to provide an improved ultrasonic diagnostic apparatus capable of automatically changing an ultrasonic wave to be transmitted according to the field of view.

SUMMARY OF THE INVENTION

The ultrasonic diagnostic apparatus of the present invention comprises ultrasonic transmitting/receiving means for transmitting an ultrasonic wave to a living body and receiving a wave reflected from the living body to convert the reflected wave into an electric signal, control means for controlling the frequency of the ultrasonic wave to be transmitted by the ultrasonic transmitting/receiving means according to a field of view, and display means for displaying a diagnostic image on the basis of the electric signal from the ultrasonic transmitting/receiving means. In this arrangement, the frequency of the ultrasonic wave to be transmitted by the ultrasonic transmitting/receiving means can be automatically changed according to the field of view.

In the ultrasonic diagnostic apparatus of the present invention, the control means may be arranged to control the frequency of the ultrasonic wave to be transmitted by the ultrasonic transmitting/receiving means according to the depth of field of view. In this arrangement, the frequency of the ultrasonic wave to be transmitted by the ultrasonic transmitting/receiving means can be automatically changed according to the depth of field of view.

In the ultrasonic diagnostic apparatus of the present invention, the control means may be arranged to control the frequency of the ultrasonic wave to be transmitted by the ultrasonic transmitting/receiving means according to the position of the enlargingly displayed area of field of view. In this arrangement, the frequency of the ultrasonic wave to be transmitted by the ultrasonic transmitting/receiving means can be automatically changed according to the position of the enlargingly displayed area of field of view.

In the ultrasonic diagnostic apparatus of the present invention, in addition to an arrangement comprising ultrasonic transmitting/receiving means for transmitting an ultrasonic wave to a living body and receiving a wave reflected from the living body to convert the reflected wave into an electric signal, control means for controlling the frequency of the ultrasonic wave to be transmitted by the ultrasonic transmitting/receiving means according to a field of view, and display means for displaying a diagnostic image on the basis of the electric signal from the ultrasonic transmitting/receiving means, the ultrasonic diagnostic apparatus may be arranged to further include a rewritable retention table for diagnostic condition data. In the arrangement, a user can change easily such a setting that the frequency of the ultrasonic wave to be transmitted by the ultrasonic transmitting/receiving means can be automatically changed according to the field of view.

BRIEF DESCRIPTION OF THE DRAWINGS

The above objects and summary of the invention will be better understood when taken in conjunction with the following detailed description and accompanying drawings, in which.

DETAILED DESCRIPTION OF THE INVENTION

Figure 1:
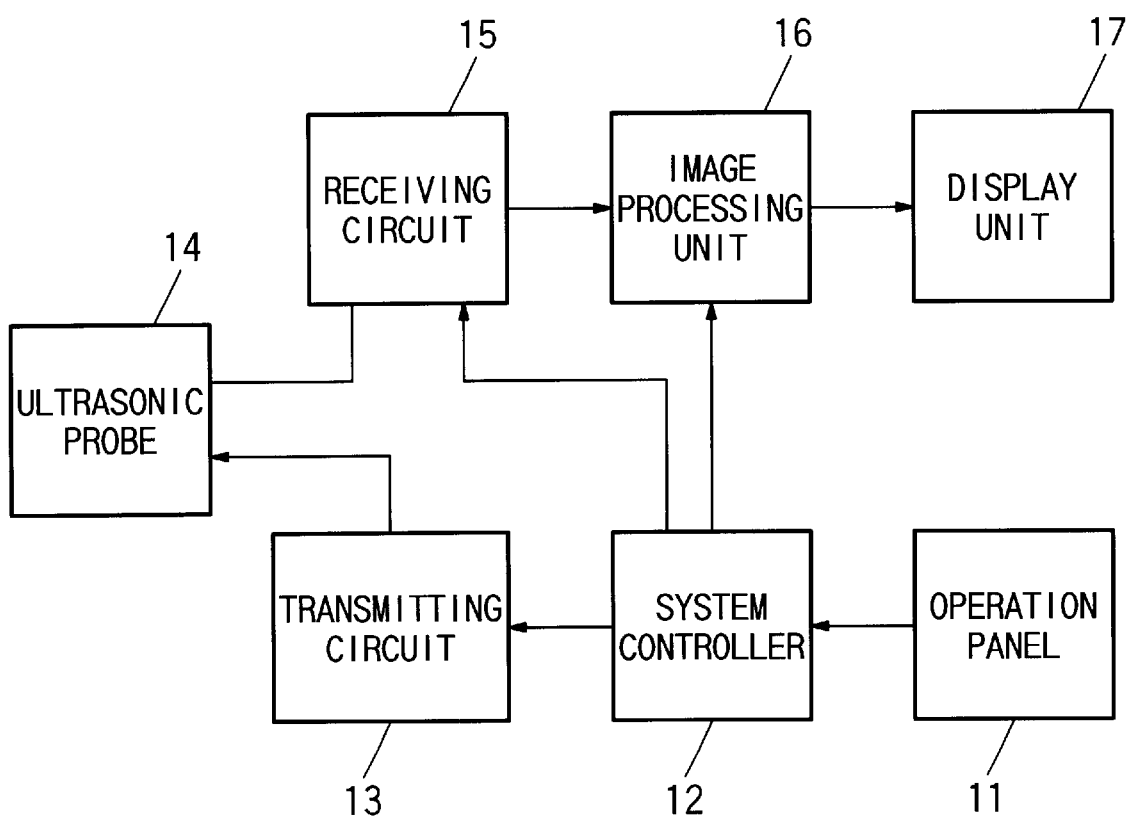
FIG. 1 shows a construction view of the first embodiment of the present invention.

The embodiments of the present invention will be described hereinafter using the drawings. FIG. 1 shows the first embodiment of the present invention. An operation panel 11 is adapted to allow a user to set different diagnostic conditions. For example, the user can make selection of diagnostic modes, etc., and settings of the depth of field of view, the enlargingly displayed area of field of view and the like. The information set through the operation panel 11 is supplied to a system controller 12.

The system controller 12 is adapted to control the whole system, particularly, to determine the frequency of the ultrasonic wave to be transmitted from an ultrasonic probe 14 according to the field of view set through the operation panel 11. The system controller 12 determines to transmit an ultrasonic wave of low frequency when the depth of field of view is set to deep level and to transmit an ultrasonic wave of high frequency when the depth of field of view is set to shallow level. The ultrasonic probe used in this embodiment has a wide frequency range or ultrasonic elements of two or more different types, for example, the ultrasonic probe is designed so that it can transmit and receive ultrasonic waves of 5.0–7.5 MHz.

Figure 2:
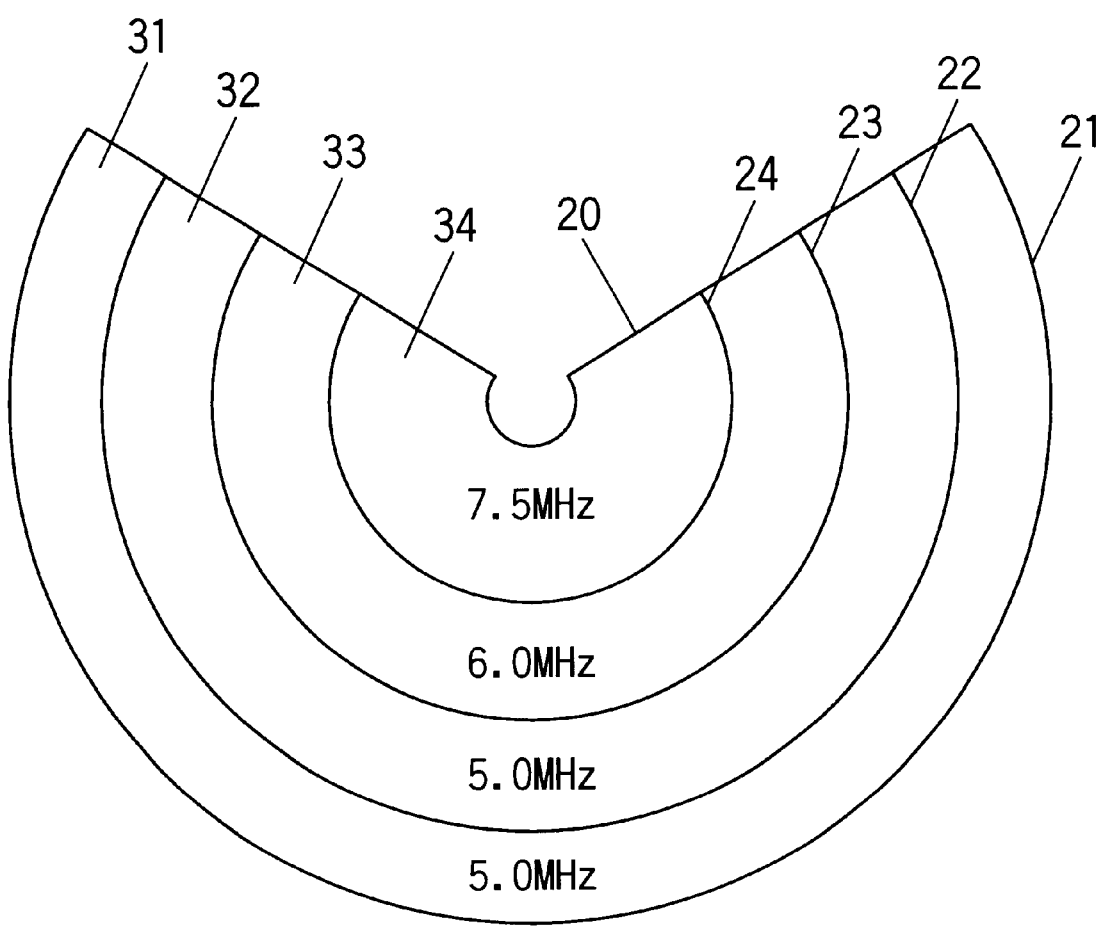
FIG. 2 show a view for illustrating the operation of the present invention.
Figure 3:
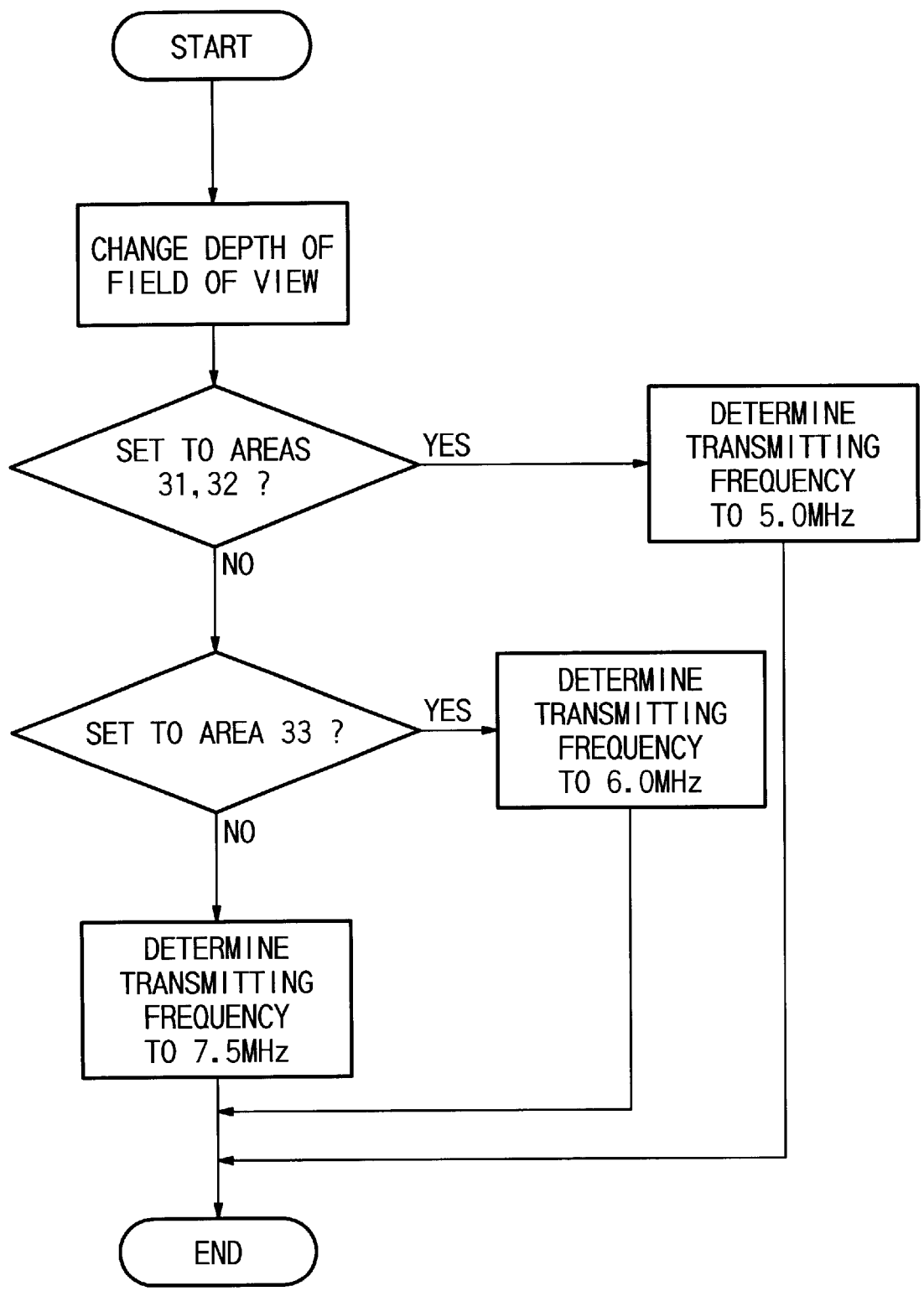
FIG. 3 shows a flowchart for illustrating the operation of the present invention.

One example of the method for determining the ultrasonic wave frequency set forth above will be described with reference to FIGS. 2 and 3. FIG. 2 shows the case of mechanical sector. In the present embodiment, the ultrasonic waves of three different frequencies of 5.0, 6.0 and 7.5 MHz are transmitted. In FIG. 2, reference numeral 20 designates the maximum field of view when the ultrasonic wave of 5.0 MHz is transmitted. Arc 21 shows the maximum depth of field of view when the ultrasonic wave 5.0 MHz is transmitted. Arcs 22, 23 and 24 show the limit of visible depth when the frequency of the ultrasonic wave is 5.0, 6.0 and 7.5 MHz respectively. Reference numerals 31, 32, 33 and 34 designate respectively the areas surrounded by these arcs 21, 22, 23 and 24. It is determined that the ultrasonic wave of 5.0 MHz is transmitted when the depth of field of view is set to the areas 31 and 32, the ultrasonic wave of 6.0 MHz is transmitted when the depth of field of view is set to the area 33, the ultrasonic wave of 7.5 MHz is transmitted when the depth of field of view is set to the area 34.

In conventional case. the limit of visible depth is the arc 23 in FIG. 2 when the ultrasonic wave of 6.0 MHz is transmitted. In the present invention, the drive frequency for the ultrasonic probe 14 is determined as set forth above, whereby the ultrasonic wave of 5.0 MHz is transmitted when the depth of field of view is set in the area 32, and as a result, the limit of visible depth becomes the arc 22. Consequently, the field of view is extended by the portion of the area 32 over the conventional apparatus. The information concerning the tissue surrounding the diagnostic target region can be obtained as an image to improve the accuracy of the diagnosis. If the depth of field of view is set to the shallow level, the ultrasonic wave of high frequency is transmitted. As a result, the resolution is improved over the conventional apparatus. The case of mechanical sector probe has been described hereinbefore and alternatively, an array probe and the like can be used. There is no limitation on the type of ultrasonic probe.

A transmitting circuit 13 generates a master signal therein and converts a trigger signal of the frequency determined by the system controller 12 into a pulse signal of high voltage on the basis of the frequency of the master signal and then the pulse signal is applied to the ultrasonic probe 14. The ultrasonic probe 14 transmits an ultrasonic wave into the living body or the organ of the patient in response to the pulse signal and receive a wave reflected from the organ of the patient and converts the reflected wave to an electric signal. This electric signal is input to a receiving circuit 15 in a back stage. The receiving circuit 15 applys the predetermined amplification and detection, etc. to the electric signal and supplies the signal to an image processing unit 16. The image processing unit 16 applies the predetermined processing to the signal from the receiving circuit 15 and displays the signal on a display unit 17 as a diagnostic image. The operation of the ultrasonic diagnostic apparatus set forth above will be described hereinafter.

A case where B mode is selected through the operation panel 11 will be described. When the depth of field of view is set through the operation panel 14, the information concerning the set depth of field of view is supplied to the system controller 12. The system controller 12 determines the driving frequency for the ultrasonic probe 14 in response to the depth of field of view. For example, the frequency is determined to be set to 5.0 MHz if the set depth of field of view is in the area 32 in FIG. 2. The information concerning the frequency is supplied to the transmitting circuit 13. The transmitting circuit 13 converts the trigger signal of the frequency determined by the system controller 12 into the pulse signal of high voltage and then, the pulse signal is applied to the ultrasonic probe 14. The ultrasonic wave transmitted from the ultrasonic probe 14 in response to the pulse signal is reflected by the different tissues of the patient body and received by the ultrasonic probe 14 and then, converted into an electric signal. This electric signal is input to the receiving circuit 15 in the back stage. The receiving circuit 15 applies amplification and detection, etc. to the electric signal and supplies the electric signal to the image processing unit 16. The image processing unit 16 implements processing such as scan transform or brightness transform to the electric signal and supplies the processed electric signal to the display unit 17 as image data. The display unit 17 displays the image data as an ultrasonic diagnostic image.

The advantage of the apparatus set forth above is that if the depth of field of view is set according to the position of diagnostic target region, an ultrasonic wave which frequency corresponds to the depth of field of view is transmitted, and therefore, information concerning the area surrounding the diagnostic target region is obtained, and if the depth of field of view is set shallow, an image of high resolution can be obtained.

Further, the advantage of the apparatus is that an ultrasonic wave which frequency corresponds to the depth of field of view is transmitted and therefore, if the depth of field of view is set deep, the limit of visible depth becomes deep whereby it becomes easy to see the diagnostic image, and as a result, the accuracy of diagnosis is improved.

Further, the advantage of the apparatus is that an ultrasonic wave which frequency corresponds to the position of enlargingly displayed area of field of view is transmitted, and therefore, if the enlargingly displayed area of field of view is set shallow, an image of high resolution can be obtained.

Further, the advantage of the apparatus is that an ultrasonic wave which frequency corresponds to the position of the enlargingly displayed area of field of view is transmitted and therefore, if the enlargingly displayed area of field of view is set deep, the limit of visible depth becomes deep, whereby it becomes easy to see the enlargingly displayed diagnostic image, and as a result, the accuracy of diagnosis is improved.

According to the embodiment as described hereinbefore, ultrasonic waves of three different frequencies are transmitted. However, it is intended to include two or more different frequencies. Further, it is not intended to limit the present invention to the embodiment described hereinbefore. Many modifications are possible within the scope of the present invention defined in the appended claims.

Figure 4:
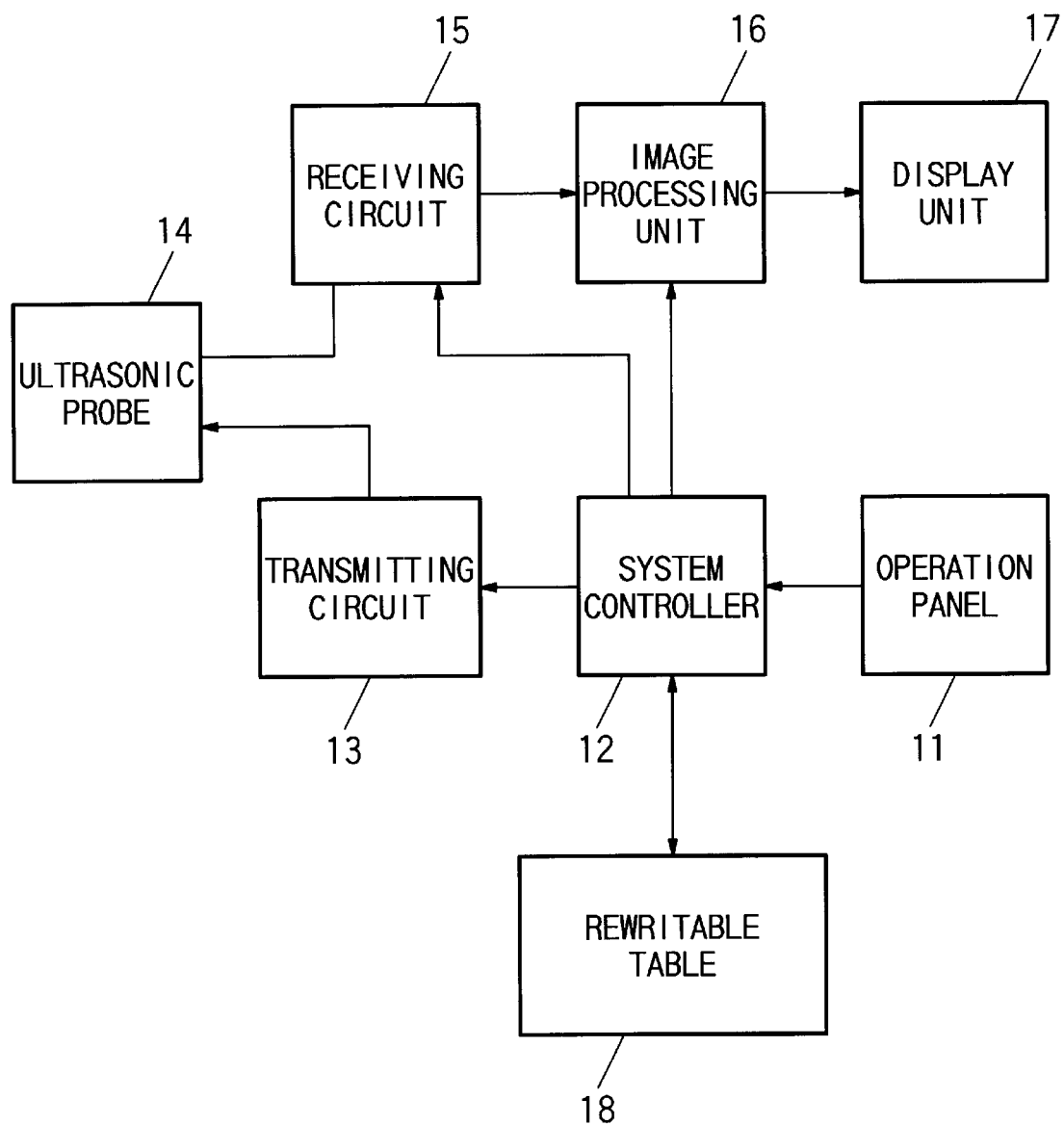
FIG. 4 shows a construction view of the second embodiment of the present invention.
Figure 5:
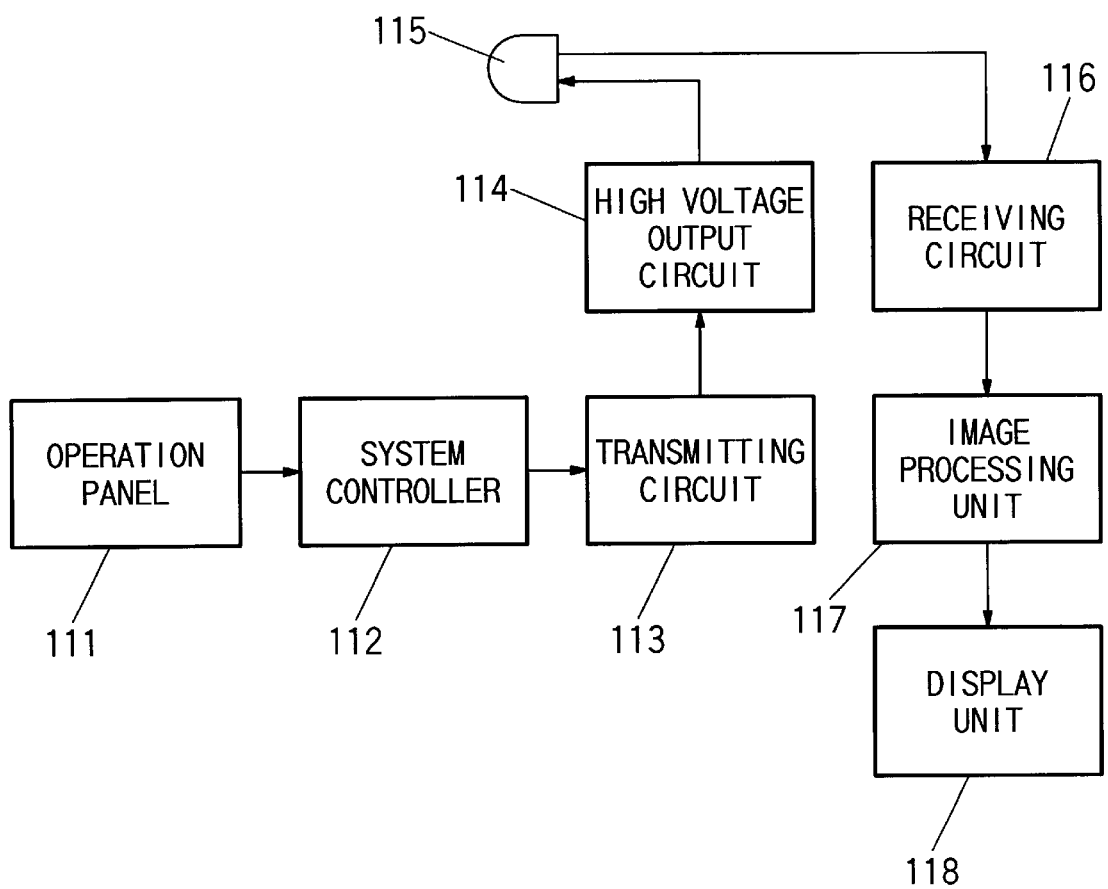
FIG. 5 shows a construction view of prior art.

The second embodiment of the present invention will be now described using FIG. 4. As shown in FIG. 4, the second embodiment of the present invention is different from the first embodiment as set forth above in further including a rewritable table 18. The content of the table displayed on the TV moniter is easily rewritable by the user through the operation panel 11. The system controller 12 checks the rewritable table 18 on the basis of the information concerning the field of view set through the operation panel 11 and controls the transmitting circuit 13 to change the frequency of the ultrasonic wave to be transmitted.

Control of the frequency of the ultrasonic wave to be transmitted with respect to the depth of field of view will be hereinafter described by way of example.

Table 1 shows one example of the contents of the rewritable table 18.

TABLE 1

| Depth Of Field Of View | Frequency Of Ultrasonic Wave To Be Transmitted |
| --- | --- |
| from 20 mm or more to less than 50 mm | 7.5 MHz |
| from 50 mm or more to less than 120 mm | 6.0 MHz |
| 120 mm or more | 5.0 MHz |

The value of the depth of field of view shown in Table 1 is displayed on the display unit 17 whereby the user can easily rewrite the value of the depth of field of view through the operation panel 11.

The degree of absorption of ultrasonic wave into the patient body varies with type of the patient body. The degree of absorption of ultrasonic wave into the patient body varies with different target organs in the diagnostic field such as abdominal area, obstetric area, etc. Since the degree of absorption of ultrasonic wave into patient body changes, the limit of visible depth also changes even if the transmitting frequency is constant.

According to this construction, the user can easily change the setting wherein the frequency of the ultrasonic wave to be transmitted from the ultrasonic transmitting/receiving means according to the field of view is automatically changed, and therefore, it is easy to compensate in response to the change of limit of visible depth.

It is possible to rewrite the value of transmitting frequency and keep storing the combination of the values. In the Table, three different ranges are set, but it is possible to set the ranges more finely. Control of the frequency of the ultrasonic wave to be transmitted is made not only in response to the depth of field of view but also in other setting such as in response to the position of the enlargingly displayed area of field of view, etc.

As described in detail above, the advantage of the present invention is that if the depth of field of view is set according to the position of diagnostic target region, an ultrasonic wave which frequency corresponds to the depth of field of view is transmitted, and therefore, information concerning the area surrounding the diagnostic target region is obtained, and if the depth of field of view is set shallow, an image of high resolution can be obtained.

Further, the advantage of the present invention is that an ultrasonic wave which frequency corresponds to the depth of field of view is transmitted and therefore, if the depth of field of view is set deep, the limit of visible depth becomes deep whereby it becomes easy to see the diagnostic image, and as a result, the accuracy of diagnosis is improved.

Further, the advantage of the present invention is that an ultrasonic wave which frequency corresponds to the position of enlargingly displayed area of field of view is transmitted, and therefore, if enlargingly displayed area of field of view is set shallow, an image of high resolution can be obtained.

Further, the advantage of the present invention is that an ultrasonic wave which frequency corresponds to the position of the enlargingly displayed area of field of view is transmitted and therefore, if the enlargingly displayed area of field of view is set deep, the limit of visible depth becomes deep, whereby it becomes easy to see the enlargingly displayed diagnostic image, and as a result, the accuracy of diagnosis is improved.

According to the present invention, the user can easily change the setting wherein the frequency of the ultrasonic wave to be transmitted from the ultrasonic transmitting/receiving means according to the field of view is automatically changed, and therefore, it is easy to compensate in response to the change of limit of visible depth.

What is claimed is:

1. An ultrasonic diagnostic apparatus comprising:
   ultrasonic transmitting/receiving means for transmitting an ultrasonic wave to a body and receiving a reflected wave from the body to convert the received reflected wave into an electric signal;
   control means for controlling a frequency of the ultrasonic wave to be transmitted from said ultrasonic transmitting/receiving means according to a depth of a field of view set by a user through an operation panel so that a single transmit frequency is selected for the depth of the field of view as the frequency of the ultrasonic wave; and,
   display means for displaying a diagnostic image based on the electric signal from said ultrasonic transmitting/receiving means.

2. The ultrasonic diagnostic apparatus described in claim 1, wherein said control means controls the frequency of the ultrasonic wave to be transmitted from said ultrasonic transmitting/receiving means according to a maximum depth of the field of view.

3. The ultrasonic diagnostic apparatus described in claim 1, wherein said control means controls the frequency of the ultrasonic wave to be transmitted by said ultrasonic transmitting/receiving means according to a position of the field of view to be enlarglingly displayed.

4. The ultrasonic diagnostic apparatus described in claim 1, further comprising a rewritable retention table for diagnostic condition data.

5. The ultrasonic diagnostic apparatus described in claim 1, wherein said ultrasonic transmitting/receiving means has an ultrasonic probe for transmitting ultrasonic waves of a plurality of different frequencies, said control means includes a system controller for determining the frequency of the ultrasonic wave to be transmitted from said ultrasonic probe according to the depth of the field of view set by the user through the operation panel, and said display means includes a display unit.

6. An ultrasonic diagnostic apparatus comprising:

a transmitter operable to transmit an ultrasonic wave to a body;

a receiver operable to receive a reflected wave from the body and to convert the received reflected wave into an electric signal;

a controller operable to control a frequency of the ultrasonic wave to be transmitted from said ultrasonic transmitter according to a depth of a field of view set by a user through an operation panel so that a single transmit frequency is selected for the depth of the field of view as the frequency of the ultrasonic wave; and a display operable to display a diagnostic image based on the electric signal from said receiver.

7. An ultrasonic diagnostic apparatus according to claim 6, wherein said controller controls the frequency of said ultrasonic wave to be transmitted from said transmitter according to a maximum depth of the field of view.

8. An ultrasonic diagnostic apparatus according to claim 6, wherein said controller controls the frequency of said ultrasonic wave to be transmitted by said transmitter according to a position of the field of view to be enlargingly displayed.

9. An ultrasonic diagnostic apparatus according to claim 6, further comprising a rewritable retention table for storing diagnostic condition data.

10. An ultrasonic diagnostic apparatus according to claim 6, further comprising an ultrasonic probe connected to said transmitter and said receiver, said ultrasonic probe being operable to transmit ultrasonic waves of a plurality of different frequencies, wherein said controller comprises a system controller operable to determine the frequency of the ultrasonic wave to be transmitted from said ultrasonic probe according to the depth of the field of view set by the user, and said display comprises a display unit.

* * * * *